United States Patent [19]

Saunders et al.

[11] 4,329,489
[45] May 11, 1982

[54] METHOD OF PREPARATION OF FLUOROCARBON COMPOUNDS

[75] Inventors: Peter R. Saunders, Richmond; Raymond J. Biron, Colonial Heights, both of Va.

[73] Assignee: Allied Chemical Corporation, Morris Township, Morris County, N.J.

[21] Appl. No.: 151,499

[22] Filed: May 19, 1980

[51] Int. Cl.³ ............................................. C07C 67/08
[52] U.S. Cl. ...................................... 560/79; 560/78; 560/87
[58] Field of Search .............................. 560/79, 87, 78

[56] References Cited

U.S. PATENT DOCUMENTS 2,921,957  1/1960  O'Rear et al. .................... 560/87
3,004,061  10/1961  Baer et al. ........................ 560/87
4,193,880  3/1980  Marshall .......................... 560/87

OTHER PUBLICATIONS

Mares et al, "Book of Papers, 1975 National Conference", AATCC Meeting, Oct. 17, 1975, pp. 270–276.

*Primary Examiner*—Nicky Chan
*Assistant Examiner*—Vera C. Clarke
*Attorney, Agent, or Firm*—Richard A. Anderson

[57] ABSTRACT

Preparation of a fluorocarbon compound used to make a soil-resistant yarn is improved by removing most of the impurities from the fluoro-carbon compound mass with heat and vacuum after the final washing step and then adding an emulsifier to the fluorocarbon compound mass so that the mass can be handled as a liquid concentrate rather than a tacky solid.

17 Claims, No Drawings

METHOD OF PREPARATION OF FLUOROCARBON COMPOUNDS

BACKGROUND OF THE INVENTION

This invention relates to an improved method of preparation of fluorocompounds. More particularly, the invention relates to use of heat and vacuum to remove impurities and adding an emulsifier to the fluorocarbon compound mass to create a concentrated liquid rather than a tacky solid product.

In recent years it has become increasingly popular to sell carpets that have been treated to resist soiling. These soil-resisting treatment products are bought by the carpet manufacturers as aqueous emulsions and are applied to the carpets by spraying as the final step in carpet manufacturing. As a result, the treatment is confined to the carpet face with fiber surfaces deep in the pile being unprotected. The face fibers are essentially sheathed with antisoiling agent but, since there is no means of binding the modifier to the fiber surface, as the surfaces are subjected to normal wear the sheath is slowly lost by abrasion.

It was discovered that the surface of Nylon 6 fibers can be altered prior to sale to a carpet manufacturer by using a properly designed fluorocarbon containing compound. The low surface energy fiber is essentially unaffected by the subsequent carpet manufacturing steps and results in an antisoiling carpet in which the complete pile is treated, not just the carpet face. This novel technology allows the fiber manufacturer complete control of the surface modification and eliminates the additional operation in the carpet manufacturer's plant.

The tetra ester of pyromellitic acid is such a fluorocarbon containing compound. See U.S. allowed Ser. No. 861,372, filed Dec. 16, 1977, now U.S. Pat. No. 4,209,610 in which two of the esters contain perfluoroalkylethyl chains and the other two contain 2-hydroxy-3-chloropropyl groups. The preferred compound is a 50—50 mixture of two isomers and hereafter will be referred to as DSR which has the following structure:

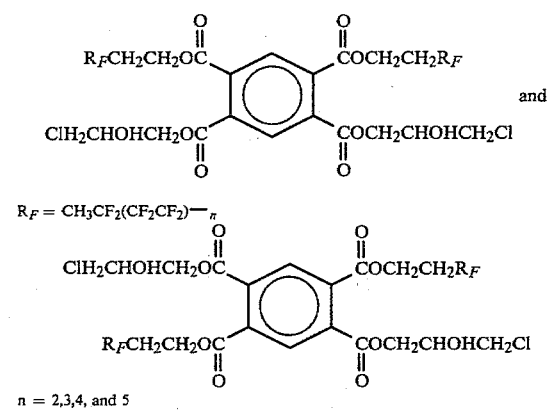

The low surface energies needed to produce a soil-repellent surface, one not wetted by either water or oil-borne stains, dictates that the surface consist of oriented fluorocarbon chains. Commercially, the fluorocarbon chains are synthesized by the telomerization of pentafluoroethyliodide and tetrafluoroethylene. The desired telomers are separated by distillation from the telomer mixture. The lower molecular weight telomers are recycled and the very small amount of higher telomers are either discarded or used for other purposes. Perfluoroalkylethanol is produced by addition of ethylene and then conversion of the perfluoroalkylethyliodide to the alcohol. Thus, steps of the laboratory synthesis are, 1. $R_FI + CH_2=CH \rightarrow R_FCH_2CH_2I$ 2. $R_FCH_2CH_2I \rightarrow R_FCH_2CH_2OH$ where $R_F = CF_2CF_2(CF_2CF_2)_n$ n=2,3,4 and 5,

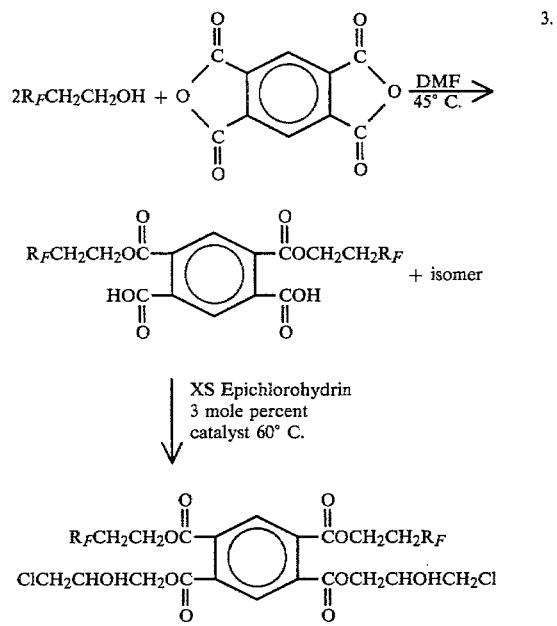

Two moles of the perfluoroalkylethanol are reacted with pyromellitic dianhydride by stirring in dimethylformamide (DMF) solution for twenty-four hours at 45° C. To the solution of the intermediate, diester-diacid, was added three moles of epichlorohydrin and three mole percent triethylamine based on the number of moles of carboxyl groups present. The temperature is raised to 60° C. and the reaction, which is complete in six to eight hours, is followed by titration of the excess epichlorohydrin with hydrogen bromide in glacial acetic acid. The reaction mixture contains about 50 percent DSR which is recovered by drowning in fifteen to twenty volumes of cold (~5° C.) water with rapid stirring. The soft particles are washed five times with equivalent volumes of cold water to remove the solvent and the epichlorohydrin. The last wash slurry is pumped to a filter. The soft tacky filter cake contains an equal weight of water and is difficult to manually transfer to drums for shipping in large quantities.

In the development of a commercial process for manufacturing DSR, a change was made in the reaction solvent from dimethylformamide (DMF) to N-methylpyrrolidone (NMP). See U.S. Ser. No. 044,880 filed June 6, 1979, hereby incorporated by reference. Analysis indicates a purer product which is reflected in greater laundry stability.

SUMMARY OF THE INVENTION

An improved procedure for recovering and handling the fluorocarbon compounds, such as DSR, has been devised. As mentioned earlier, the common laboratory procedure for recovering the DSR is to pour the reaction mixture into fifteen to twenty volumes of rapidly stirred water. The water is removed by decanting and the soft tacky particles of DSR are washed four or five times with equivalent volumes of water. The last wash is filtered and the soft, tacky filter cake contains about fifty weight percent water. Since all wash waters must be treated to chemically destroy the excess epichlorohydrin and subsequently passed through a holding point to allow biodegradation of the organics, limiting the amount of wash water is very desirable. It has been found that after precipitation, one or two water washes will remove most of the unreacted epichlorohydrin and the N-methylpyrrolidone solvent. After decanting the water from the second wash cycle, the wet product in the wash kettle is subjected to vacuum distillation. Vacuums of one Torr to seven hundred Torr and temperatures from 60° C. to 150° C. could be used without adversely affecting the product. The preferred temperature range is between 90° C. to 110° C. The preferred vacuum range is between five Torr to two hundred Torr. Essentially all water, epichlorohydrin and even some of the N-methylpyrrolidone can be removed. The DSR is allowed to cool to about 80° C. and the surfactant used in preparing the emulsions used to incorporate the DSR in a yarn spin finish is added. This emulsion concentrate is then easily pumped into drums for shipping. Typical product specifications are seventy percent DSR, less than one percent water, less than a quarter of a percent N-methylpyrrolidone and less than one part per million epichlorohydrin.

This invention is an improvement in the preparation of a fluorocarbon compound having the formula

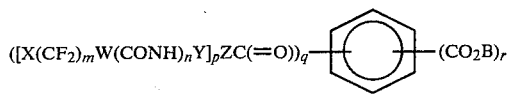

$([X(CF_2)_mW(CONH)_nY]_pZC(=O))_q$—⬡—$(CO_2B)_r$ wherein the attachment of the fluorinated radicals and the radicals $CO_2B$ to the nucleus is in asymmetrical positions with respect to rotation about the axis through the center of the nucleus wherein "X" is fluorine, or perfluoroalkoxy of 1 to 6 carbon atoms, and m has arithmetic mean between 2 and 20; n is zero or unity; "W" and "Y" are alkylene, cycloalkylene or alkyleneoxy radicals of combined chain length from 2 to 20 atoms; $(CF_2)_m$ and "Y" have each at least 2 carbon atoms in the main chain; "Z" is oxygen and p is 1, or "Z" is nitrogen and p is 2; q is an integer of at least 2 but not greater than 5; "B" is $CH_2RCHOH$ or is $CH_2RCHOCH_2RCHOH$ where "R" is hydrogen or methyl, or "B" is $CH_2CH(OH)CH_2Q$ where Q is halogen, hydroxy, or nitrile; or "B" is $CH_2CH(OH)CH_2OCH_2CH(OH)CH_2Q$; and r is an integer of at least 1 but not greater than q; and $X(CH_2)_m$, W and Y are straight chains, branched chains or cyclic; and wherein the substituent chains of the above general formulas are the same or different. The improvement comprises removing most of the impurities from the fluorocarbon mass with heat and vacuum after the final washing step, then adding an emulsifier to the fluorocarbon compound mass so that the mass can be handled as a liquid concentrate rather than a tacky solid. Preferred emulsifier is a solution consisting essentially of about 40 to 90 percent by weight of a salt of dioctyl sulfosuccinate, about 5 to 30 percent by weight of propylene glycol and about 5 to 30 percent by weight of water. The most preferred emulsifier is a solution consisting essentially of about 70 percent by weight of sodium dioctyl sulfosuccinate, about 16 percent by weight of propylene glycol, and about 14 percent by weight of water. In general, the impurities removed from the fluorocarbon compound mass are water, solvent and epichlorohydrin. The solvent can be n-methylpyrrolidone, dimethylformamide or a saturated aliphatic ester having a boiling point between about 80° and 150° C. See U.S. Ser. No. 88,989 filed Oct. 29, 1979, now U.S. Pat. No. 4,252,982, hereby incorporated by reference. The impurities are removed generally by heat and vacuum. Preferably the heat is at a temperature of from about 100° to 150° C. and the vacuum is from between 5 to 200 Torr. Application of heat and vacuum is for a time sufficient to lower the water content to below 1.5 percent, preferably reduced to below one percent by weight. In the most preferred process, the molten mass of the fluorocarbon compound is allowed to cool to 75° to 95° C. and the emulsifier is added to the molten mass of the fluorocarbon compound at a ratio of 10:4 parts fluorocarbon compound to emulsifier by weight by stirring at 75° to 95° C. for 0.5 to 1 hour.

In a more specific preparation of bis(perfluoroalkylethyl)bis(2-hydroxy-3-chloropropyl)tetra ester of pyromellitic acid (DSR) is improved by removing most of the impurities from the fluoro-carbon mass with heat and vacuum after the final washing step, then adding an emulsifier to the fluorocarbon compound mass so that the mass of DSR can be handled as a liquid concentrate rather than a tacky solid. The same preferred emulsifier as described above is preferred in this process also. In all the above processes, it is preferred to use the same emulsifier to emulsify the fluorocarbon chemical into a concentrated liquid as is used for adding the fluorocarbon compound, such as DSR, to a spin finish for application to synthetic filaments during spinning of the molten synthetic polymer into filaments of fiber. This results in a soil-resistant yarn for carpets and other applications.

EXAMPLE

The final step in the prior art preparation of DSR is the removal of water from the semi-solid press cake. This process involves loss of the expensive product during transfer from the reaction vessel to the filter press and further losses in the filter press. In addition, the final product contains 30-50 percent water which imposes serious restraints on the process used to prepare the finish emulsion. In addition, undesirable impurities such as epichlorohydrin and NMP may be present unless exhaustive washing is employed.

This invention involves the following:

(1) After washing, instead of separating the DSR by filtration, the contents of the reaction vessel which is stirred are heated to temperatures up to 100° C. and a vacuum of less than 200 Torr is applied to the vessel. This continues until the water content of the DSR has been reduced to 0.2 percent or less.

(2) The vacuum is released and while continuing to stir the molten DSR is allowed to cool to 75°–95° C. Then for each 100 parts by weight of DSR, 40 parts by weight of Aerosol OT 70PG is added. Stirring continues for 0.5–1 hour while the temperature is maintained at 75°–95° C. The fluid DSR concentrate is then discharged into drums.

The product contains no detectable epichlorohydrin and the NMP is less than 0.25 percent and usually 0.05 percent. Water is present at 6-9 percent which came from the water in the Aerosol OT 70PG. Fluoroalcohol concentration varies from 0.5 to 2.0 percent and most often is 1 percent.

The concentrate on heating to 90° C. and the addition of an additional 10 parts by weight of Aerosol OT 70PG to each 100 parts by weight of DSR is immediately available for conversion into a spin finish.

ADVANTAGES OF INVENTION (1) DSR yield is improved.
(2) Epichlorohydrin is completely removed.
(3) NMP and excess fluoroalcohol are reduced to a minimum.
(4) The concentration of water in the product is reduced to a low uniform level which makes possible a consistent process for spin finish preparation.

Aerosol OT 70PG, a tradename of American Cyanamid Company, Wayne, New Jersey is 80 percent by weight of sodium dioctyl sulfosuccinate, 16 percent by weight of propylene glycol, and 14 percent by weight of water. The use of this emulsifier in the yarn spin finish for coating yarn to make it soil resistant is the subject of U.S. Pat. No. 4,192,754, hereby incorporated by reference.

The above Aerosol OT 70PG is preferred in this invention, however, other emulsifiers, useful in making spin finish emulsions, could also be used. See U.S. Pat. Nos. 4,193,880 and 4,134,839, both hereby incorporated by reference.

We claim:
1. In the preparation, by the reaction of a perfluoroalkylethanol and pyromellitic dianhydride and subsequent conversion of pendent carboxyl groups to the alkyl ester-$(CO_2B)_r$, of a fluorocarbon compound having the formula

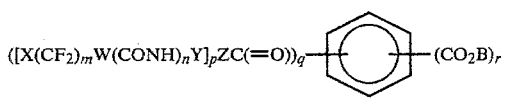

wherein the attachment of the fluorinated radicals and the radicals $CO_2B$ to the nucleus is in asymmetrical positions with respect to rotation about the axis through the center of the nucleus wherein "X" is fluorine, or perfluoroalkoxy of 1 to 6 carbon atoms, and m has arithmetic mean between 2 and 20; n is zero or unity; "W" and "Y" are alkylene, cycloalkylene or alkyleneoxy radicals of combined chain length from 2 to 20 atoms; $(CF_2)_m$ and "Y" have each at least 2 carbon atoms in the main chain; "Z" is oxygen and p is 1, or "Z" is nitrogen and p is 2; q is an integer of at least 2 but not greater than 5; "B" is $CH_2RCHOH$ or is $CH_2RCHOCH_2RCHOH$ where "R" is hydrogen or methyl, or "B" is $CH_2CH(OH)CH_2Q$ where Q is halogen, hydroxy, or nitrile; or "B" is $CH_2CH(OH)CH_2OCH_2CH(OH)CH_2Q$; and r is an integer of at least 1 but not greater than q; and $X(CF_2)_m$, W and Y are straight chains, branched chains or cyclic; and wherein the substituent chains of the above general formulas are the same or different, the improvement comprising
removing most of the impurities from the fluorocarbon mass with heat and vacuum after the final washing step, then
adding an emulsifier to the fluorocarbon compound mass
so that the mass can be handled as a liquid concentrate rather than a tacky solid.

2. The preparation of claim 1 wherein the emulsifier is a solution consisting essentially of about 40 to 90 percent by weight of a salt of dioctyl sulfosuccinate, about 5 to 30 percent by weight of propylene glycol and about 5 to 30 percent by weight of water.

3. In the preparation of the fluorocarbon compound of claim 1 wherein the fluorocarbon compound is a mixture of pyromellitates having the structure:

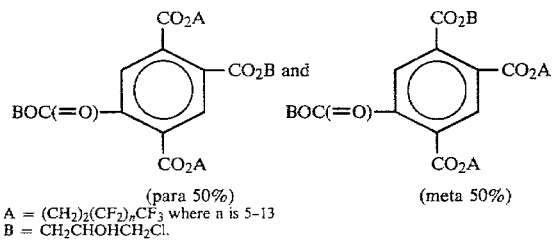

(para 50%)   (meta 50%)
A = $(CH_2)_2(CF_2)_nCF_3$ where n is 5-13
B = $CH_2CHOHCH_2Cl$.

4. The preparation of claim 3 wherein the emulsifier is a solution consisting essentially of about 70 percent by weight of sodium dioctyl sulfosuccinate, about 16 percent by weight of propylene glycol and about 14 percent by weight of water.

5. The preparation of claim 3 wherein the impurities are water, solvent and epichlorohydrin.

6. The preparation of claim 5 wherein the solvent is N-methylpyrrolidone.

7. The preparation of claim 5 wherein the solvent is dimethylformamide.

8. The preparation of claim 5 wherein the solvent is a saturated aliphatic ester having a boiling point between about 50° and 150° C.

9. The preparation of claim 1 wherein the heat is at a temperature from about 60° to about 150° C. and the vacuum is between about one Torr to seven hundred Torr.

10. The preparation of claim 1 wherein the temperature is between about 90° to 110° C.

11. The preparation of claim 1 wherein the vacuum is from between 5 to 200 Torr.

12. The preparation of claim 1 wherein the application of heat and vacuum is sufficient to lower the water content to below 1.5 percent.

13. The preparation of claim 12 wherein the water content is reduced to below one percent by weight.

14. The preparation of claim 13 wherein the molten mass of the fluorocarbon compound is allowed to cool to 75° to 95° C. and the emulsifier is added to the molten mass of fluorocarbon compound at a ratio of about 10 to 4 parts fluorocarbon compound to emulsifier by weight by stirring at 75° to 95° C. for 0.5 to 1 hour.

15. The preparation of claim 14 wherein the emulsifier is a solution consisting essentially of about 40 to 90 percent by weight of a salt of dioctyl sulfosuccinate, about 5 to 30 percent by weight of propylene glycol and about 5 to 30 percent by weight of water.

16. In the preparation of the fluorocarbon compound of claim 1, wherein the fluorocarbon compound is bis(-perfluoroalkylethyl)-bis-(2-hydroxy-3-chloropropyl)-tetraester of pyromellitic acid (DSR).

17. The preparation of claim 16 wherein the emulsifier used is the same emulsifier used for adding the DSR to a spin finish for application to synthetic filaments during spinning of the molten synthetic polymer into filaments.

* * * * *